United States Patent [19]

Osborn

[11] 4,197,858
[45] Apr. 15, 1980

[54] SENSING LIQUID TRAP FOR RESPIRATORY GAS ANALYZING SYSTEMS

[75] Inventor: John J. Osborn, Tiburon, Calif.

[73] Assignee: Research Development Corporation, San Francisco, Calif.

[21] Appl. No.: 894,190

[22] Filed: Apr. 6, 1978

[51] Int. Cl.$^2$ .............................................. A61B 5/08
[52] U.S. Cl. .................................... 128/718; 128/719; 73/421.5 R; 340/620; 422/84
[58] Field of Search ..................... 128/2.07, 2.08, 2 C, 128/718, 730, 719; 73/421.5 R; 23/232 E, 232 E; 422/83, 84; 55/215; 340/618, 620

[56] References Cited

U.S. PATENT DOCUMENTS

| | | | |
|---|---|---|---|
| 3,000,377 | 9/1961 | Tolbert et al. | 128/2.07 |
| 3,257,782 | 6/1966 | Weiss | 73/421.5 R |
| 3,339,578 | 9/1967 | Smith | 340/620 X |
| 3,395,699 | 8/1968 | Beasley | 128/2.08 |

FOREIGN PATENT DOCUMENTS 1040284  10/1958  Fed. Rep. of Germany ............. 422/83

Primary Examiner—Lee S. Cohen
Attorney, Agent, or Firm—Flehr, Hohbach, Test, Albritton & Herbert

[57] ABSTRACT

A trap for collecting liquid in a gas line between the patient and a respiratory gas analyzer which trap senses the collection of a predetermined volume of liquid and operates upon sensing that volume to immediately interrupt the connection between the gas analyzer and the deposit of liquid and also to initiate a flushing cycle such that the liquid is flushed out of the lines to protect the analyzer from contamination.

6 Claims, 2 Drawing Figures

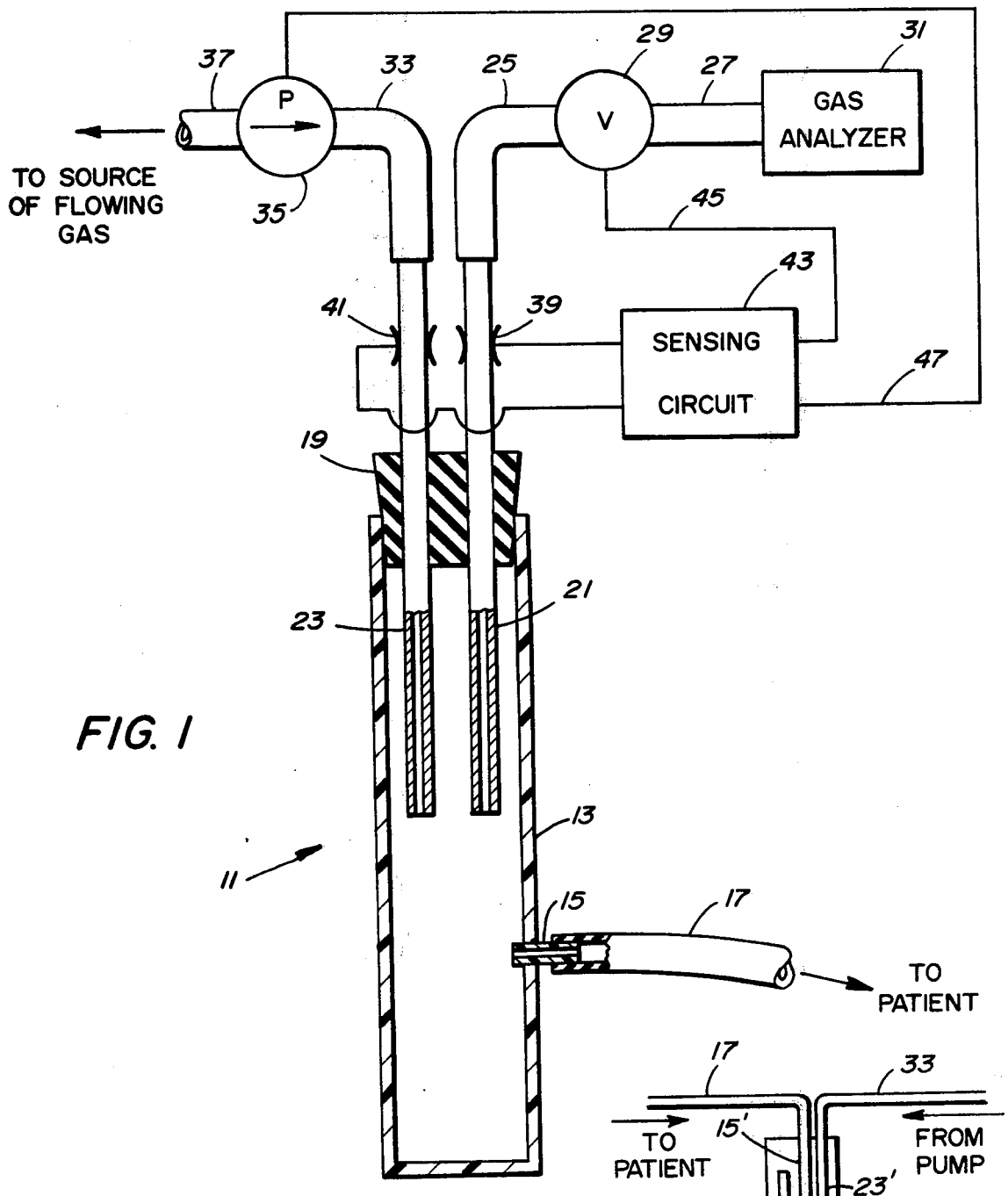

SENSING LIQUID TRAP FOR RESPIRATORY GAS ANALYZING SYSTEMS

BACKGROUND OF THE INVENTION

Although reliable and rapid response carbon dioxide gas meters for respiratory measurements have been developed for more than twenty-five years, such meters have not been widely used for respiratory monitoring. Although the continuous measurement of respiratory $CO_2$ concentration is very useful in the care of patients undergoing anesthesia, or on mechanical respirators, a practical method of making the measurement continuously for long periods has not been achieved because the airway of a patient is fully saturated with water vapor and often contains frank water and mucous. The high humidity of the air being sampled leads to condensation in the sampling line, or in the gas analyzer itself, and thus greatly alters the response of the analyzer. Of course, this is even more serious if water or mucous are drawn through the tract of the analyzer. For these reasons continuous monitoring of the ariway $CO_2$ concentration has usually required continued attention to the prevention of condensation and has been subject to great inaccuracies whenever the sampling line drew in water, or mucous coughed up by the patient.

In the past it has been impractical to place a moisture trap in the sampling line to collect water inadvertently enteing the line before it could reach the analyzer. This has been due to the fact that it is important to maintain laminar flow in the sampling system to as great an extent as possible. Any amount of deadspace throughout the line, even though very small, will allow intermixing of the gases and reduce the specific response of the analyzer. A trap small enough not to degrade the signal is too small to entrap any reasonably large amount of water.

There have been other problems with using the traps in the past. The trap should be disposable so that it can be discarded and replaced with a new one if it should fill with liquid. However, in most carbon dioxide sampling systems, the lines are flushed automatically every few minutes to prevent the build up of condensation. Moreover, bacterial contamination from one patient to the next is possible if that flushing takes place through a partially contaminated trap. So the disposable trap must be arranged such that it is impossible for contamination from one patient to be transferred to a subsequent patient by those portions of the sampling system which are not disposable or which cannot be sterilized.

SUMMARY OF THE INVENTION

The invention is embodied in a trap comprising a relatively small, container having connected thereto a first tube to be coupled to the patient for drawing the gases to be sampled, a second tube to be connected to the gas analyzer conducting samples of gases thereto and a third line connected to a source of flushing air or other gas. Electrically conductive probe means which may be two of the connecting tubes themselves, are connected to a sensing circuit which is activated upon the level of liquid within the container reaching the probe. When activated, the sensing circuit closes a valve in the line between the trap and the gas analyzer. The sensing circuit may also initiate operation of a pump to force flushing gas through the trap and the line to the patient.

BRIEF DESCRIPTION OF THE DRAWING

FIG. 1 is a schematic diagram of a sensing fluid trap in accordance with the preferred embodiment of the invention.

FIG. 2 is a schematic diagram of an alternative form of trap.

DETAILED DESCRIPTION OF THE INVENTION

Referring to FIG. 1 there is shown a trap 11 comprising a container 13 formed of nonelectrically conductive material such as plastic and having a very small volume, for instance, less than five milliliters. The trap includes a first line 15 which is connected to a tube 17 placed in communication with the patient whose respiratory gas is to be analyzed. A lid or stopper 19 closes the container 13 and carries two additional tubes 21 and 23 which are preferably of electrically conducting material such as metal. The tubes 21 and 23 then serve not only as conduits but also as electrical probes as will be seen hereinafter.

Tube 21 is connected by means of lines 25, 27 and electrically operated valve 29 to a gas analyzer 31. The tube 23, on the other hand, is connected by means of a line 33 to a pump 35. The inlet of the pump 35 is in communication with the atmosphere, or some other source of flushing gas, gas through the line 37.

The trap 11 is held in position by engagement of tubes 21 and 23 in their respective electrical contact clamps 39 and 41. Contacts 39 and 41 are in turn coupled to a sensing circuit 43, the output of which is connected by lines 45 and 47 to the electrically operable valve 29 and the pump 35 respectively.

In operation, the line 17 receives sampling gases from the patient and transmits them through the tube 15 to the small container 13 from which they are drawn by the gas analyzer 31 through the tube 21, the lines 25 and 27 and the valve 29. So long as the container 13 is free of moisture the gas analyzer 31 continues to draw gases from the patient's airway through the trap 11 for continuous analysis. However, if and when water enters the container 13 and rises to a level sufficient to contact the tubes 21 and 23, the electrical resistance between those tubes is substantially reduced and that resistance is sensed by the sensing circuit 43. Sensing circuit 43, in a manner well known in the art operates upon sensing that lowered resistance to initiate an electrical output along the line 45 to immediately activate the valve 29 and interrupt communication between the tube 21 and the gas analyzer 31. The gas analyzer 31 is thereby protected from any water which might reach the trap 11. The sensing circuit 43, upon sensing the lower resistance between the tubes 21 and 23, may also initiate an electrical output along the line 47 to operate the pump 35. Operation of the pump 35 then forces a flow of flushing air or gas through the tube 23, container 13, the tube 15 and the line 17 back to the patient. Since the amount of liquid within the trap 11 is so small, the flow of flushing gas can be quite low so that the flushing action toward the patient and the reverse flow of the fluid through that line 17 are not even noticed by the patient and have no adverse effect.

The trap 11 together with its connecting lines 17, 25 and 33 are disposable and can be changed each time the system is used. To assure that proper contact is made with the clamps 39 and 41 those clamps serve the dual purpose of electrical contact and holder for the trap 11.

Thus, the trap cannot be positioned without making contact with its electrodes. The design of the trap also serves to allow separation of the sample and flush lines so that, within the unsterilized analyzer, tubing which has handled inlet air and is possibly contaminated, is entirely separate from tubing which handles flush air going toward the patient. So long as a sterile protecting trap is used the patient is safe from contamination.

Referring to FIG. 2, an alternative form of trap is shown wherein the only difference from that shown in FIG. 1 is the placement of the tubes 15', 21' and 23' corresponding to tubes 15, 21 and 23 of FIG. 1. Thus it is seen that the positioning of the tubes within the trap may take many forms and any two of the three may serve as the electrically conductive probe means.

What is claimed is:

1. A liquid trap for use with respiratory gas analysis systems comprising a container, a first fluid line connected to said container and adapted to be placed in communication with a patient, a second fluid line connected to said container and adapted to be connected to a gas analyzer, an electrically operated valve in said second fluid line, electrical probe means in said container for sensing a predetermined level of liquid therein, sensing circuit means having an input coupled to said probe means and output means coupled to said electrically operated valve, said sensing circuit means being operable in response to the attainment of said predetermined level of liquid to close said electrically operated valve, a third fluid line connected to said container and adapted to be connected to a source of flushing gas, and an electrically operated pump in said third fluid line, said sensing circuit means being further operable when said predetermined level has been reached to commence operation of said electrically operated pump.

2. A liquid trap as defined in claim 1 wherein said container has a volume no greater than five milliliters.

3. A liquid trap as defined in claim 1 wherein said electrical probe means includes an electrically conductive tube connected to one of said fluid lines a portion of said electrically conductive tube being disposed within said container.

4. A liquid trap as defined in claim 1 wherein said electrical probe means includes two electrically conductive tubes, each of said electrically conductive tubes being connected to one of said fluid lines, a portion of each of said electrically conductive tubes being disposed within said container, said container being formed of an electrically non-conductive material.

5. A liquid trap as defined in claim 1, together with electrically conductive clamp means adapted to receive said electrical probe means, said electrically conductive clamp means being connected to the input of said sensing circuit means.

6. A liquid trap for use with respiratory gas analysis systems comprising a container, a first fluid line connected to said container and adapted to be placed in communication with a patient, a second fluid line connected to said container and adapted to be connected to a gas analyzer, an electrically operated valve in said second fluid line, electrical probe means in said container for sensing a predetermined level of liquid therein, said electrical probe means including two electrically conductive tubes, each of said electrically conductive tubes being connected to one of said fluid lines, a portion of each of said electrically conductive tubes being disposed within said container, said container being formed of an electrically non-conductive material, sensing circuit means having an input coupled to said probe means and output means coupled to said electrically operated valve, said sensing circuit means being operable in response to the attainment of said predetermined level of liquid to close said electrically operated valve.

* * * * *